United States Patent
Pugh et al.

(10) Patent No.: US 9,323,073 B2
(45) Date of Patent: Apr. 26, 2016

(54) ELECTRONIC OPHTHALMIC LENS WITH EMITTER-DETECTOR PAIR SENSOR

(71) Applicants: Randall Braxton Pugh, St. Johns, FL (US); Adam Toner, Jacksonville, FL (US); Daniel B. Otts, Fruit Cove, FL (US)

(72) Inventors: Randall Braxton Pugh, St. Johns, FL (US); Adam Toner, Jacksonville, FL (US); Daniel B. Otts, Fruit Cove, FL (US)

(73) Assignee: Johnson & Johnson Vision Care, Inc.

( * ) Notice: Subject to any disclaimer, the term of this patent is extended or adjusted under 35 U.S.C. 154(b) by 534 days.

(21) Appl. No.: 13/780,194

(22) Filed: Feb. 28, 2013

(65) Prior Publication Data

US 2014/0240657 A1  Aug. 28, 2014

(51) Int. Cl.
  G02C 7/04  (2006.01)
  G02C 7/08  (2006.01)
  A61F 2/16  (2006.01)

(52) U.S. Cl.
  CPC .............. *G02C 7/083* (2013.01); *A61F 2/1624* (2013.01); *G02C 7/04* (2013.01); *G02C 7/081* (2013.01)

(58) Field of Classification Search
  CPC .......... G02C 27/04; G02C 7/049; G02C 7/02; G02C 7/06
  USPC .............. 351/159.02, 159.03, 159.04, 159.05
  See application file for complete search history.

(56) References Cited

U.S. PATENT DOCUMENTS

| | | | |
|---|---|---|---|
| 2004/0027536 A1* | 2/2004 | Blum | B29D 11/00826 351/159.03 |
| 2006/0155372 A1 | 7/2006 | Coroneo | |
| 2008/0106633 A1 | 5/2008 | Blum et al. | |
| 2009/0103044 A1 | 4/2009 | Duston et al. | |
| 2009/0204207 A1 | 8/2009 | Blum et al. | |
| 2012/0310339 A1* | 12/2012 | Berge | G02C 7/085 623/6.22 |
| 2013/0035760 A1 | 2/2013 | Portney | |
| 2014/0327875 A1* | 11/2014 | Blum | A61F 2/1618 351/159.03 |

FOREIGN PATENT DOCUMENTS

| | | |
|---|---|---|
| WO | WO 2004/015460 A2 | 2/2004 |
| WO | WO 2004/067391 A2 | 8/2004 |
| WO | WO2006/050171 A2 | 2/2006 |
| WO | WO 2011/067391 A1 | 6/2011 |

OTHER PUBLICATIONS

European Search Report for Application No. EP14157312 completed May 27, 2014.
Patent Examination Report issued by the Australian Government dated May 1, 2014 for corresponding Application No. 2013204447.
Search Report issued by the Intellectual Property Office of Singapore dated Aug. 8, 2014 for Application No. 2013021423.
Examination Report issued by the Australian Patent Office for corresponding Application No. 201304447 dated May 1, 2014.

* cited by examiner

*Primary Examiner* — Ricky Mack
*Assistant Examiner* — Robert E Tallman
(74) *Attorney, Agent, or Firm* — Carl J. Evens

(57) ABSTRACT

An emitter-detector pair sensor may be incorporated into a powered or electronic ophthalmic lens. The emitter-detector pair sensor may be configured to determine the distance from the sensor to an object in its path. Based upon this information, a system controller of the ophthalmic lens may output a signal to an actuator of the ophthalmic lens to control a variable power optic of the ophthalmic lens.

13 Claims, 12 Drawing Sheets

ELECTRONIC OPHTHALMIC LENS WITH EMITTER-DETECTOR PAIR SENSOR

BACKGROUND OF THE INVENTION

1. Field of the Invention

The present invention relates to a powered or electronic ophthalmic lens having a sensor and associated hardware and software for detecting or determining the distance to nearby objects, and more particularly, to a powered or electronic ophthalmic lens having a sensor and associated hardware and software for detecting or determining the distance to nearby objects to change the focal lengths of a variable power optic.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance performance of the eye. In another example, either with or without adjustable focus, a wearable contact lens may incorporate electronic sensors to detect concentrations of particular chemicals in the precorneal (tear) film. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

The human eye has the ability to discern millions of colors, adjust easily to shifting light conditions, and transmit signals or information to the brain at a rate exceeding that of a high-speed internee connection. Lenses, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Contact lenses may be utilized to correct myopia, hyperopia, astigmatism as well as other visual acuity defects. Contact lenses may also be utilized to enhance the natural appearance of the wearer's eyes. Contact lenses or "contacts" are simply lenses placed on the anterior surface of the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeability and are generally more comfortable to wear than the contact lenses made of the earlier hard materials.

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contract lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and Internet access. The lenses may be designed to allow the wearer to see in low-light conditions. The properly designed electronics and/or arrangement of electronics on lenses may allow for projecting an image onto the retina, for example, without a variable-focus optic lens, provide novelty image displays and even provide wakeup alerts, Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This, coupled with a wireless data transmitter, could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The proper combination of devices could yield potentially unlimited functionality; however, there are a number of difficulties associated with the incorporation of extra components on a piece of optical-grade polymer. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters of a transparent polymer while protecting the components from the liquid environment on the eye. It is also difficult to make a contact lens comfortable and safe for the wearer with the added thickness of additional components.

Given the area and volume constraints of an ophthalmic device such as a contact lens, and the environment in which it is to be utilized, the physical realization of the device must overcome a number of problems, including mounting and interconnecting a number of electronic components on a non-planar surface, the bulk of which comprises optic plastic.

Accordingly, there exists a need for providing a mechanically and electrically robust electronic contact lens.

As these are powered lenses, energy or more particularly current consumption, to run the electronics is a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption, for example, up to eighteen (18) hours on a single charge, after potentially remaining idle for years. Accordingly, there exists a need for a system that is optimized for low-cost, long-term reliable service, safety and size while providing the required power.

In addition, because of the complexity of the functionality associated with a powered lens and the high level of interaction between all of the components comprising a powered lens, there is a need to coordinate and control the overall operation of the electronics and optics comprising a powered ophthalmic lens. Accordingly, there is a need for a system to control the operation of all of the other components that is safe, low-cost, and reliable, has a low rate of power consumption and is scalable for incorporation into an ophthalmic lens.

Powered or electronic ophthalmic lenses may have to account for certain unique physiological functions from the individual utilizing the powered or electronic ophthalmic lens. More specifically, powered lenses may have to account for blinking, including the number of blinks in a given time period, the duration of a blink, the time between blinks and any number of possible blink patterns, for example, if the individual is dosing off. Blink detection may also be utilized to provide certain functionality, for example, blinking may be utilized as a means to control one or more aspects of a powered ophthalmic lens. Additionally, external factors, such as changes in light intensity levels, and the amount of visible light that a person's eyelid blocks out, have to be accounted for when determining blinks. For example, if a room has an illumination level between fifty-four (54) and one hundred sixty-one (161) lux, a photosensor should be sensitive enough to detect light intensity changes that occur when a person blinks.

Ambient light sensors or photosensors are utilized in many systems and products, for example, on televisions to adjust brightness according to the room light, on lights to switch on at dusk, and on phones to adjust the screen brightness. However, these currently utilized sensor systems are not small enough and/or do not have low enough power consumption for incorporation into contact lenses.

It is also important to note that different types of blink detectors may be implemented with computer vision systems directed at one's eye(s), for example, a camera digitized to a computer. Software running on the computer can recognize visual patterns such as the eye open and closed. These systems may be utilized in ophthalmic clinical settings for diagnostic purposes and studies. Unlike the above described detectors and systems, these systems are intended for off eye use and to look at rather than look away from the eye. Although these systems are not small enough to be incorporated into contact lenses, the software utilized may be similar to the software that would work in conjunction with powered contact lenses. Either system may incorporate software implementations of artificial neural networks that learn from input and adjust their output accordingly. Alternately, non-biology based software implementations incorporating statistics, other adaptive algorithms, and/or signal processing may be utilized to create smart systems.

Accordingly, there exists a need for a means and method for detecting certain physiological functions, such as a blink, and utilizing them to activate and/or control an electronic or powered ophthalmic lens according to the type of blink sequence detected by a sensor. The sensor being utilized having to be sized and configured for use in a contact lens.

Emitter-detector pairs are common in various fields/technologies and are utilized for detecting the presence and location of objects. For example, infrared (IR) light-emitting diode (LED) emitters are coupled with semiconductor detectors to determine proximity of a hand to a paper towel or soap dispenser. Emitter-detector pairs are also common in presence sensing for room illumination and alarm systems, for example, triggering lights to be on when a user enters a room or an alarm when an intruder enters. Such systems may comprise global IR illumination and an IR camera, whereas other systems may comprise tighter coupling between the emitter and detector, for example, a narrow-field IR emitter which only couples to a sensor within a few inches and is time-synchronized with the detector.

Emitter-detector pairs are also common in photography and videography. Ultrasonic systems may be used to determine the location of objects in camera autofocus systems. Other autofocus systems may be employed with ambient and/or emitted light, for example, contrast detection algorithms may be applied to a series of images acquired by image sensors as the focal length of a lens is swept. In some cases of low illumination, the camera will emit a flash or beam of light and record the reflection to determine if the image to be captured is in focus. If not, the camera will command a servo to change the focal length on the objective lens.

Determining the location of an object may be useful for determining the desired focal distance for an ophthalmic lens comprising a variable power optic, for example, determining if a presbyopic user of the lens intends to focus on an up-close book or a distant road sign. Emitter-detectors could therefore be useful in electronic ophthalmic devices. However, existing emitter-detector pairs are not well suited for use in electronic or powered ophthalmic lenses. Accordingly, there exists a need for an emitter-detector pair having the required characteristics for incorporation into an ophthalmic lens, including the physical size, current and/or power consumption, association with eye gaze as well as numerous other factors.

SUMMARY OF THE INVENTION

The electronic ophthalmic lens with emitter-detector pair sensor in accordance with the present invention overcomes the limitations associated with the prior art as briefly described above.

In accordance with one aspect, the present invention is directed to a powered ophthalmic lens. The powered ophthalmic lens comprises a contact lens including an optic zone and a peripheral zone, and an emitter-detector pair sensor system incorporated into the peripheral zone of the contact lens, the emitter-detector pair sensor system comprising an emitter for sending out a signal, a detector for capturing a reflection of the signal, a controller operatively associated with the emitter and detector configured to determine the distance between the contact lens and an object and output a control signal based on the determined distance, and at least one actuator configured to receive the control signal and implement a predetermined function.

In accordance with another aspect, the present invention is directed to a powered ophthalmic lens. The powered ophthalmic lens comprises a contact lens, and an emitter-detector pair sensor system incorporated into the contact lens, the emitter-detector pair sensor system comprising an emitter for sending out a signal, a detector for capturing a reflection of the signal, a controller operatively associated with the emitter and detector configured to determine the distance between the contact lens and an object and output a control signal based on the determined distance, and at least one actuator configured to receive the control signal and implement a predetermined function.

In accordance with yet another aspect, the present invention is directed to a powered ophthalmic lens. The powered ophthalmic lens comprises an intraocular lens, and an emitter-detector pair sensor system incorporated into the intraocular lens, the emitter-detector pair sensor system comprising an emitter for sending out a signal, a detector for capturing a reflection of the signal, a controller operatively associated with the emitter and detector configured to determine the distance between the contact lens and an object and output a control signal based on the determined distance, and at least one actuator configured to receive the control signal and implement a predetermined function.

The present invention relates more generally to a powered contact lens comprising an electronic system, which performs any number of functions, including actuating a variable-focus optic if included. The electronic system includes one or more batteries or other power sources, power management circuitry, one or more sensors, clock generation circuitry, control algorithms and circuitry, and lens driver circuitry.

In a newborn, the crystalline lens of the eye is somewhat soft and pliant making it extremely flexible and capable of a large degree of accommodation or focusing. As a person ages, the crystalline lens gradually becomes more rigid, and thus, their eyes are less able to accommodate, or bend the natural lens, to focus on objects that are relatively near to the observer. This condition is known as presbyopia.

A plus power lens may be utilized to restore the focusing power lost by the crystalline lens. The plus power lens may take the form of reading glasses, bifocal glasses or trifocal glasses. Reading glasses are easily utilized when an individual does not need refractive correction for distance. However, distant objects will be blurry when looking through reading glasses. If an individual is already wearing glasses for myopia, hyperopia and/or astigmatism, then the plus power may be added to the existing glasses in the form of a bifocal or trifocal lens. Contact lenses may also be worn to address presbyopia. In one type of such lenses, distance and near vision regions are concentrically arranged around the geometric center of the lens. Light passing though the optical zone of the lens is concentrated and focused at more than one point in the eye. These lenses are generally used in simultaneous vision mode. In simultaneous vision, portions of the lens optical zone focused for distance and near are available at the same time, focusing light from both object distances simultaneously. This is disadvantageous as image quality and image contrast may be degraded.

In another type of contact lens; namely, a segmented lens, near and distance vision regions are not concentric about the geometric center of the lens. The wearer of the segmented lenses is able to access the near vision region of the lens because the lens is constructed to allow it to translate, or move vertically relative to the pupil of the wearer's eye. This translating lens moves vertically when the person wearing the lens shifts their gaze downwardly, for example, to read. This upwardly positions the near vision portion in the center of the wearer's gaze. Substantially all of the light passing though the optical zone may be focused at a single point in the eye based on gaze.

An electronic or powered ophthalmic lens or more particularly, an electronic or powered contact lens may, as stated above, perform any number of functions, including actuating a variable power optic. Accordingly, if a powered ophthalmic lens comprises a variable power optic, the individual wearing the lens would be able to increase his or her add power for viewing near distance objects or alternatively to decrease his or her add power for viewing far distance objects. In other words, a powered contact lens would provide an extraordinary benefit to an individual with presbyopia. Control over the variable power optic may be achieved in a number of ways. In accordance with the present invention, an emitter-detector pair sensor may be incorporated into the contact lens to automatically control the variable power optic. Emitter-detector pair sensors are devices that simply emit signals from an emitter circuit that bounce off an object in the signals path and are captured by a detector circuit. From a knowledge of the energy transmitted and the time elapsed from emission to detection, the distance from the emitter-detector pair sensor to the object may be determined. This information may be input to a system controller of the powered contact lens which commands an actuator to adjust the variable power optic accordingly.

An infrared emitter-detector pair sensor may be particularly advantageous for basic object or obstacle detection and easy to implement. The present invention takes this basic circuit and implements it for incorporation into a contact lens.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
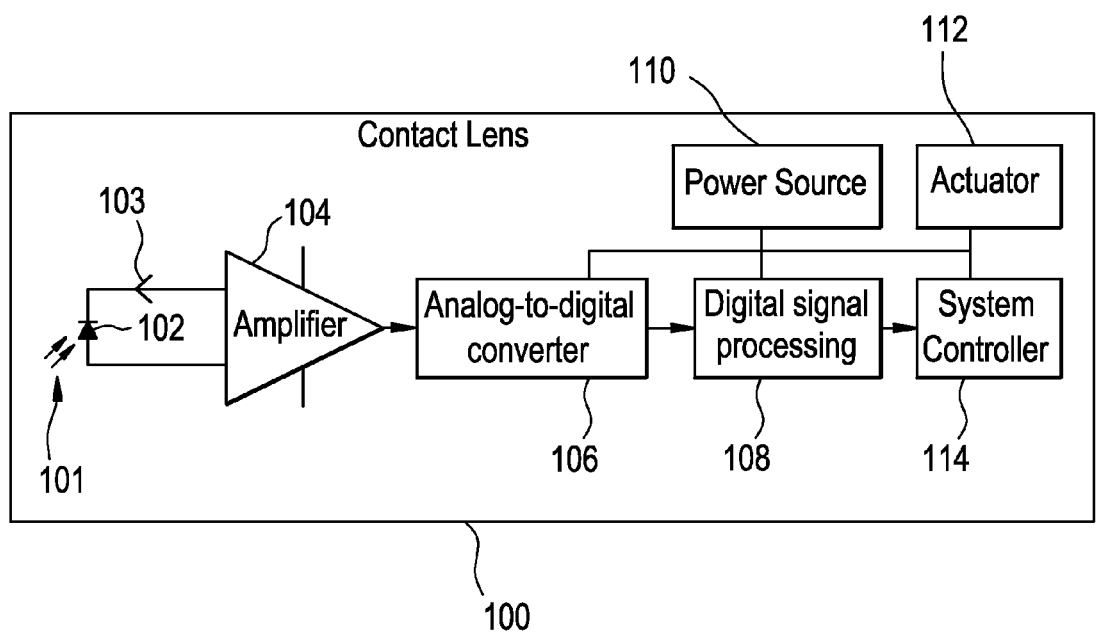
FIG. 1 illustrates an exemplary contact lens comprising a blink detection system in accordance with some embodiments of the present invention.

Conventional contact lenses are polymeric structures with specific shapes to correct various vision problems as briefly set forth above. To achieve enhanced functionality, various circuits and components may be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contact lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This coupled with a wireless data transmitter could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The powered or electronic contact lens of the present invention comprises the necessary elements to correct and/or enhance the vision of patients with one or more of the above described vision defects or otherwise perform a useful ophthalmic function. In addition, the electronic contact lens may be utilized simply to enhance normal vision or provide a wide variety of functionality as described above. The electronic contact lens may comprise a variable focus optic lens, an assembled front optic embedded into a contact lens or just simply embedding electronics without a lens for any suitable functionality. The electronic lens of the present invention may be incorporated into any number of contact lenses as described above. In addition, intraocular lenses may also incorporate the various components and functionality described herein. However, for ease of explanation, the disclosure will focus on an electronic contact lens to correct vision defects intended for single-use daily disposability.

The present invention may be employed in a powered ophthalmic lens or powered contact lens comprising an electronic system, which actuates a variable-focus optic or any other device or devices configured to implement any number of numerous functions that may be performed. The electronic system includes one or more batteries or other power sources, power management circuitry, one or more sensors, clock generation circuitry, control algorithms and circuitry, and lens driver circuitry. The complexity of these components may vary depending on the required or desired functionality of the lens.

Control of an electronic or a powered ophthalmic lens may be accomplished through a manually operated external device that communicates with the lens, such as a hand-held remote unit. For example, a fob may wirelessly communicate with the powered lens based upon manual input from the wearer. Alternately, control of the powered ophthalmic lens may be accomplished via feedback or control signals directly from the wearer. For example, sensors built into the lens may detect blinks and/or blink patterns. Based upon the pattern or sequence of blinks, the powered ophthalmic lens may change state, for example, its refractive power in order to either focus on a near object or a distant object.

Alternately, blink detection in a powered or electronic ophthalmic lens may be used for other various uses where there is interaction between the user and the electronic contact lens, such as activating another electronic device, or sending a command to another electronic device. For example, blink detection in an ophthalmic lens may be used in conjunction with a camera on a computer wherein the camera keeps track of where the eye(s) moves on the computer screen, and when the user executes a blink sequence that it detected, it causes the mouse pointer to perform a command, such as double-clicking on an item, highlighting an item, or selecting a menu item.

A blink detection algorithm is a component of the system controller which detects characteristics of blinks, for example, is the lid open or closed, the duration of the blink, the inter-blink duration, and the number of blinks in a given time period. The algorithm in accordance with the present invention relies on sampling light incident on the eye at a certain sample rate. Pre-determined blink patterns are stored and compared to the recent history of incident light samples. When patterns match, the blink detection algorithm may trigger activity in the system controller, for example, to activate the lens driver to change the refractive power of the lens.

Blinking is the rapid closing and opening of the eyelids and is an essential function of the eye. Blinking protects the eye from foreign objects, for example, individuals blink when objects unexpectedly appear in proximity to the eye. Blinking provides lubrication over the anterior surface of the eye by spreading tears. Blinking also serves to remove contaminants and/or irritants from the eye. Normally, blinking is done automatically, but external stimuli may contribute as in the case with irritants. However, blinking may also be purposeful, for example, for individuals who are unable to communicate verbally or with gestures can blink once for yes and twice for no. The blink detection algorithm and system of the present invention utilizes blinking patterns that cannot be confused with normal blinking response. In other words, if blinking is to be utilized as a means for controlling an action, then the particular pattern selected for a given action cannot occur at random; otherwise inadvertent actions may occur. As blink speed may be affected by a number of factors, including fatigue, eye injury, medication and disease, blinking patterns for control purposes preferably account for these and any other variables that affect blinking. The average length of involuntary blinks is in the range of about one hundred (100) to four hundred (400) milliseconds. Average adult men and women blink at a rate of ten (10) involuntary blinks per minute, and the average time between involuntary blinks is about 0.3 to seventy (70) seconds.

An exemplary embodiment of the blink detection algorithm may be summarized in the following steps.

1. Define an intentional "blink sequence" that a user will execute for positive blink detection.
2. Sample the incoming light level at a rate consistent with detecting the bank sequence and rejecting involuntary blinks.
3. Compare the history of sampled light levels to the expected "blink sequence," as defined by a blink template of values.
4. Optionally implement a blink "mask" sequence to indicate portions of the template to be ignored during comparisons, e.g. near transitions. This may allow for a user to deviate from a desired "blink sequence," such as a plus or minus one (1) error window, wherein one or more of lens activation, control, and focus change can occur. Additionally, this may allow for variation in the user's timing of the blink sequence.

An exemplary blink sequence may be defined as follows:
1. blink (closed) for 0.5 s
2. open for 0.5 s
3. blink (dosed) for 0.5 s At a one hundred (100) ma sample rate, a twenty (20) sample blink template is given by
   blink_template=[1,1,1, 0,0,0,0,0, 1,1,1,1,1, 0,0,0,0,0, 1,1].

The blink mask is defined to mask out the samples just after a transition (0 to mask out or ignore samples), and is given by
   blink_mask=[1,1,1, 0,1,1,1,1, 0,1,1,1,1, 0,1,1,1,1, 0,1].

Optionally, a wider transition region may be masked out to allow for more timing uncertainty, and is given by
   blink_mask=[1,1,0, 0,1,1,1,0, 0,1,1,1,0, 0,1,1,1,0, 0,1].

Alternate patterns may be implemented, e.g. single long blank, in this case a 1.5 s blink with a 24-sample template, given by
   blink_template=[1,1,1,1,0,0, 0,0,0,0,0,0, 0,0,0,0,0,0, 0,1, 1,1,1,1].

It is important to note that the above example is for illustrative purposes and does not represent a specific set of data.

Detection may be implemented by logically comparing the history of samples against the template and mask. The logical operation is to exclusive-OR (XOR) the template and the sample history sequence, on a bitwise basis, and then verify that all unmasked history bits match the template. For example, as illustrated in the blink mask samples above, in each place of the sequence of a blink mask that the value is logic 1, a blink has to match the blink mask template in that place of the sequence. However, in each place of the sequence of a blink mask that the value is logic 0, it is not necessary that a blink matches the blink mask template in that place of the sequence. For example, the following Boolean algorithm equation, as coded in MATLAB®, may be utilized.

matched=not (blink_mask)|not (xor (blink_template, test_sample)), wherein test_sample is the sample history. The matched value is a sequence with the same length as the blink template, sample history and blink_mask. If the matched sequence is all logic 1's, then a good match has occurred. Breaking it down, not (xor (blink_template, test_sample)) gives a logic 0 for each mismatch and a logic 1 for each match. Logic oring with the inverted mask forces each location in the matched sequence to a logic 1 where the mask is a logic 0. Accordingly, the more places in a blink mask template where the value is specified as logic 0, the greater the margin of error in relation to a person's blinks is allowed. MATLAB® is a high level language and implementation for numerical computation, visualization and programming and is a product of Math-Works, Natick, Mass. It is also important to note that the greater the number of logic 0's in the blink mask template, the greater the potential for false positive matched to expected or intended blink patterns. It should be appreciated that a variety of expected or intended blink patterns may be programmed into a device with one or more active at a time. More specifically, multiple expected or intended bunk patterns may be utilized for the same purpose or functionality, or to implement different or alternate functionality. For example, one bunk pattern may be utilized to cause the lens to zoom in or out on an intended object while another blink pattern may be utilized to cause another device, for example, a pump, on the lens to deliver a dose of a therapeutic agent.

FIG. 1 illustrates, in block diagram form, a contact lens 100, comprising an electronic blink detector system, in accordance with an exemplary embodiment of the present invention. In this exemplary embodiment, the electronic blink detector system may comprise a photosensor 102, an amplifier 104, an analog-to-digital converter or ADC 106, a digital signal processor 108, a power source 110, an actuator 112, and a system controller 114.

When the contact lens 100 is placed onto the front surface of a user's eye the electronic circuitry of the blink detector system may be utilized to implement the blink detection algorithm of the present invention. The photosensor 102, as well as the other circuitry, is configured to detect blinks and/or various blink patterns produced by the user's eye.

In this exemplary embodiment, the photosensor 102 may be embedded into the contact lens 100 and receives ambient light 101, converting incident photons into electrons and thereby causing a current, indicated by arrow 103, to flow into the amplifier 104. The photosensor or photodetector 102 may comprise any suitable device. In one exemplary embodiment, the photosensor 102 comprises a photodiode. In a preferred exemplary embodiment, the photodiode is implemented in a complimentary metal-oxide semiconductor (CMOS process technology) to increase integration ability and reduce the overall size of the photosensor 102 and the other circuitry. The current 103 is proportional to the incident light level and decreases substantially when the photodetector 102 is covered by an eyelid. The amplifier 104 creates an output proportional to the input, with gain, and may function as a transimpedance amplifier which converts input current into output voltage. The amplifier 104 may amplify a signal to a useable level for the remainder of the system, such as giving the signal enough voltage and power to be acquired by the ADC 106. For example, the amplifier may be necessary to drive subsequent blocks since the output of the photosensor 102 may be quite small and may be used in low-light environments. The amplifier 104 may be implemented as a variable-gain amplifier, the gain of which may be adjusted by the system controller 114, in a feedback arrangement, to maximize the dynamic range of the system. In addition to providing gain, the amplifier 104 may include other analog signal conditioning circuitry, such as filtering and other circuitry appropriate to the photosensor 102 and amplifier 104 outputs. The amplifier 104 may comprise any suitable device for amplifying and conditioning the signal output by the photosensor 102. For example, the amplifier 104 may simply comprise a single operational amplifier or a more complicated circuit comprising one or more operational amplifiers. As set forth above, the photosensor 102 and the amplifier 104 are configured to detect and isolate blink sequences based upon the incident light intensity received through the eye and convert the input current into a digital signal usable ultimately by the system controller 114. The system controller 114 is preferably preprogrammed or preconfigured to recognize various blink sequences and/or blink patterns in various light intensity level conditions and provide an appropriate output signal to the actuator 112. The system controller 114 also comprises associated memory.

In this exemplary embodiment, the ADC 106 may be used to convert a continuous, analog signal output from the amplifier 104 into a sampled, digital signal appropriate for further signal processing. For example, the ADC 106 may convert an analog signal output from the amplifier 104 into a digital signal that may be useable by subsequent or downstream circuits, such as a digital signal processing system or microprocessor 108. A digital signal processing system or digital signal processor 108 may be utilized for digital signal processing, including one or more of filtering, processing, detecting, and otherwise manipulating/processing sampled data to permit incident light detection for downstream use. The digital signal processor 108 may be preprogrammed with the blink sequences and/or blink patterns described above. The digital signal processor 108 also comprises associated memory. The digital signal processor 108 may be implemented utilizing analog circuitry, digital circuitry, software, or a combination thereof. In the illustrate exemplary embodiment, it is implemented in digital circuitry. The ADC 106 along with the associated amplifier 104 and digital signal processor 108 are activated at a suitable rate in agreement with the sampling rate previously described, for example every one hundred (100) ms.

A power source 110 supplies power for numerous components comprising the blink detection system. The power may be supplied from a battery, energy harvester, or other suitable means as is known to one of ordinary skill in the art. Essentially, any type of power source 110 may be utilized to provide reliable power for all other components of the system. A blink sequence may be utilized to change the state of the system and/or the system controller. Furthermore, the system controller 114 may control other aspects of a powered contact lens depending on input from the digital signal processor 108, for example, changing the focus or refractive power of an electronically controlled lens through the actuator 112.

Figure 2:
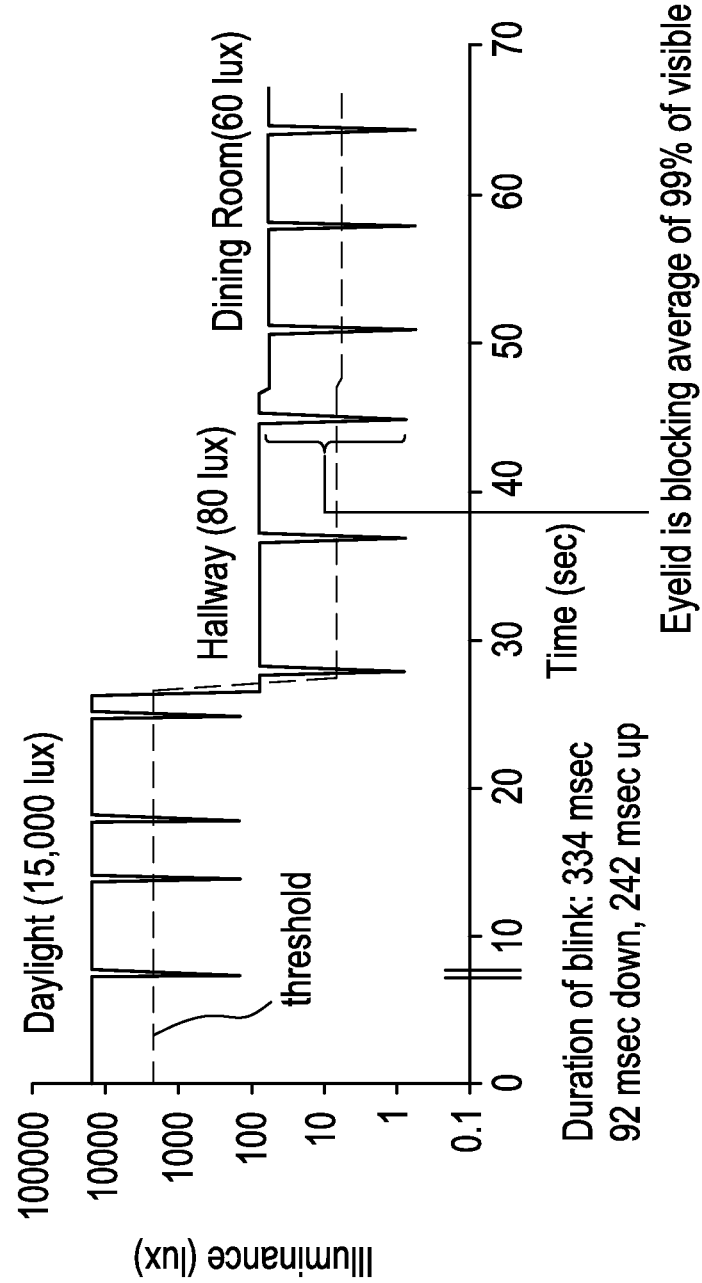
FIG. 2 illustrates a graphical representation of light incident on the surface of the eye versus time, illustrating a possible involuntary blink pattern recorded at various light intensity levels versus time and a usable threshold level based on some point between the maximum and minimum light intensity levels in accordance with the present invention.

The system controller 114 uses the signal from the photosensor chain; namely, the photosensor 102, the amplifier 104, the ADC 106 and the digital signal processing system 108, to compare sampled light levels to blink activation patterns. Referring to FIG. 2, a graphical representation of blink pattern samples recorded at various light intensity levels versus time and a usable threshold level is illustrated. Accordingly, accounting for various factors may mitigate and/or prevent error in detecting blinks when sampling light incident on the eye, such as accounting for changes in light intensity levels in different places and/or while performing various activities. Additionally, when sampling light incident on the eye, accounting for the effects that changes in ambient light intensity may have on the eye and eyelid may also mitigate and/or prevent error in detecting blinks, such as how much visible light an eyelid blocks when it is closed in low-intensity light levels and in high-intensity light levels. In other words, in order to prevent erroneous blinking patterns from being utilized to control, the level of ambient light is preferably accounted for as is explained in greater detail below.

For example, in a study, it has been found that the eyelid on average blocks approximately ninety-nine (99) percent of visible light, but at lower wavelengths less light tends to be transmitted through the eyelid, blocking out approximately 99.6 percent of visible light. At longer wavelengths, toward the infrared portion of the spectrum, the eyelid may block only thirty (30) percent of the incident light. What is important to note; however, is that light at different frequencies, wavelengths and intensities may be transmitted through the eyelids with different efficiencies. For example, when looking at a bright light source, an individual may see red light with his or her eyelids closed. There may also be variations in how much visible light an eyelid blocks based upon an individual, such as an individual's skin pigmentation. As is illustrated in FIG. 2, data samples of blink patterns across various lighting levels are simulated over the course of a seventy (70) second time interval wherein the visible light intensity levels transmitted through the eye are recorded during the course of the simulation, and a usable threshold value is illustrated. The threshold is set at a value in between the peak-to-peak value of the visible light intensity recorded for the sample blink patterns over the course of the simulation at varying light intensity levels. Having the ability to preprogram blink patterns while tracking an average light level over time and adjusting a threshold may be critical to being able to detect when an individual is blinking, as opposed to when an individual is not blinking and/or there is just a change in light intensity level in a certain area.

Referring now again to FIG. 1, in further alternate exemplary embodiments, the system controller 114 may receive input from sources including one or more of a blink detector, eye muscle sensors, and a fob control. By way of generalization, it may be obvious to one skilled in the art that the method of activating and/or controlling the system controller 114 may require the use of one or more activation methods. For example, an electronic or powered contact lens may be programmable specific to an individual user, such as programming a lens to recognize both of an individual's blink patterns and an individual's ciliary muscle signals when performing various actions, for example, focusing on an object far away, or focusing on an object that is near. In some exemplary embodiments, using more than one method to activate an electronic contact lens, such as blink detection and ciliary muscle signal detection, may give the ability for each method to be crosschecked with another before activation of the contact lens occurs. An advantage of crosschecking may include mitigation of false positives, such as minimizing the chance of unintentionally triggering a lens to activate. In one exemplary embodiment, the crosschecking may involve a voting scheme, wherein a certain number of conditions are met prior to any action taking place.

The actuator 112 may comprise any suitable device for implementing a specific action based upon a received command signal. For example, if a blink activation pattern is matched compared to a sampled light level as described above, the system controller 114 may enable the actuator 112, such as a variable-optic electronic or powered lens. The actuator 112 may comprise an electrical device, a mechanical device, a magnetic device, or any combination thereof. The actuator 112 receives a signal from the system controller 114 in addition to power from the power source 110 and produces some action based on the signal from the system controller 114. For example, if the system controller 114 signal is indicative of the wearer trying to focus on a near object, the actuator 112 may be utilized to change the refractive power of the electronic ophthalmic lens, for example, via a dynamic multi-liquid optic zone. In an alternate exemplary embodiment, the system controller 114 may output a signal indicating that a therapeutic agent should be delivered to the eye(s). In this exemplary embodiment, the actuator 112 may comprise a pump and reservoir, for example, a microelectromechanical system (MEMS) pump. As set forth above, the powered lens of the present invention may provide various functionality; accordingly, one or more actuators may be variously configured to implement the functionality.

Figure 3:
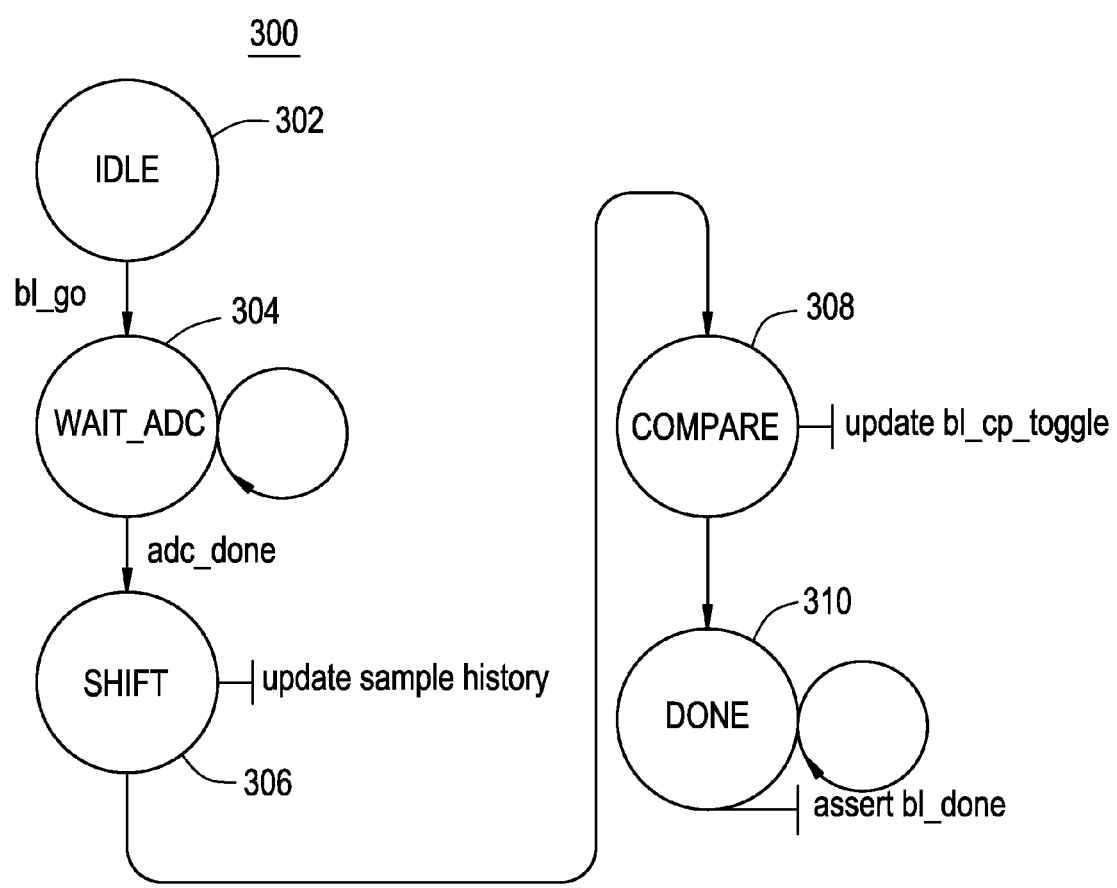
FIG. 3 is an exemplary state transition diagram of a blink detection system in accordance with the present invention.

FIG. 3 illustrates a state transition diagram 300 for an exemplary blink detection system in accordance with the blink detection algorithm of the present invention. The system starts in an IDLE state 302 waiting for an enable signal bl_go to be asserted. When the enable bl_go signal is asserted, for example, by an oscillator and control circuit which pulses bl_go at a one hundred (100) ms rate commensurate with the blink sampling rate, the state machine then transitions to a WAIT_ADC state 304 in which an ADC is enabled to convert a received light level to a digital value. The ADC asserts an adc_done signal to indicate its operations are complete, and the system or state machine transitions to a SHIFT state 306. In the SHIFT state 306 the system pushes the most recently received ADC output value onto a shift register to hold the history of blink samples. In some exemplary embodiments, the ADC output value is first compared to a threshold value to provide a single bit (1 or 0) for the sample value, in order to minimize storage requirements. The system or state machine then transitions to a COMPARE state 308 in which the values in the sample history shift register are compared to one or more blink sequence templates and masks as described above. If a match is detected, one or more output signals may be asserted, such as one to toggle the state of the lens driver, bl_cp_toggle, or any other functionality to be performed by the powered ophthalmic lens. The system or state machine then transitions to the DONE state 310 and asserts a bl_done signal to indicate its operations are complete.

Figure 4:
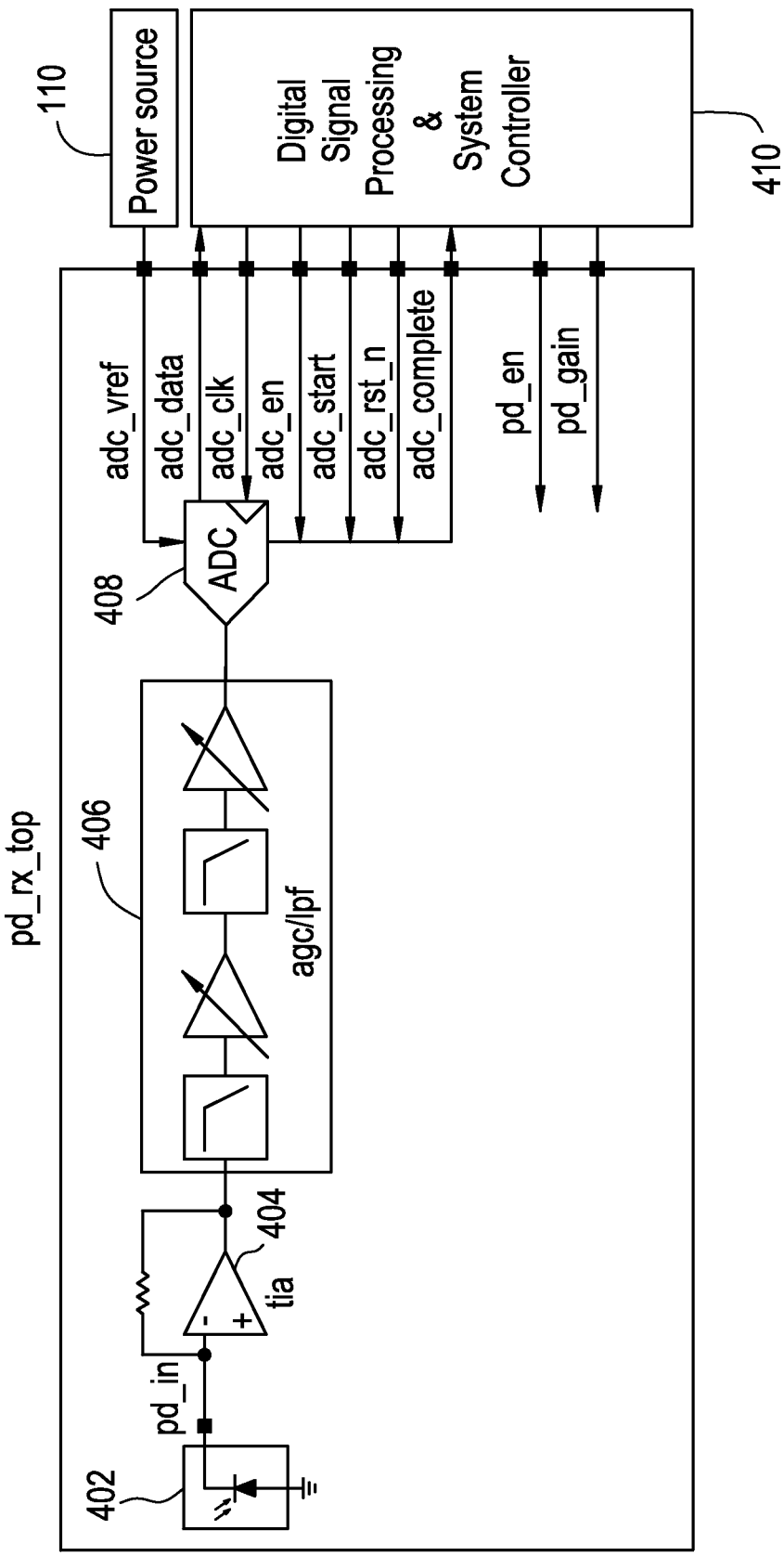
FIG. 4 is a diagrammatic representation of a photodetection path utilized to detect and sample received light signals in accordance with the present invention.

FIG. 4 illustrates an exemplary photosensor or photodetector signal path pd_rx_top that may be used to detect and sample received light levels. The signal path pd_rx_top may comprise a photodiode 402, a transimpedance amplifier 404, an automatic gain and low pass filtering stage 406 (AGC/LPF), and an ADC 408. The adc_vref signal is input to the ADC 408 from the power source 110 (see FIG. 1) or alternately it may be provided from a dedicated circuit inside the analog-to-digital converter 408. The output from the ADC 408, adc_data, is transmitted to the digital signal processing and system controller block 108/114 (see FIG. 1). Although illustrated in FIG. 1 as individual blocks 108 and 114, for ease of explanation, the digital signal processing and system controller are preferably implemented on a single block 410. The enable signal, adc_en, the start signal, adc_start, and the reset signal, adc_rst_n are received from the digital signal processing and system controller 410 while the complete signal, adc_complete, is transmitted thereto. The clock signal, adc_clk, may be received from a clock source external to the signal path, pd_rx_top, or from the digital signal processing and system controller 410. It is important to note that the adc_clk signal and the system clock may be running at different frequencies. It is also important to note that any number of different ADCs may be utilized in accordance with the present invention which may have different interface and control signals but which perform a similar function of providing a sampled, digital representation of the output of the analog portion of the photosensor signal path. The photodetect enable, pd_en, and the photodetect gain, pd_gain, are received from the digital signal processing and system controller 410.

Figure 5:
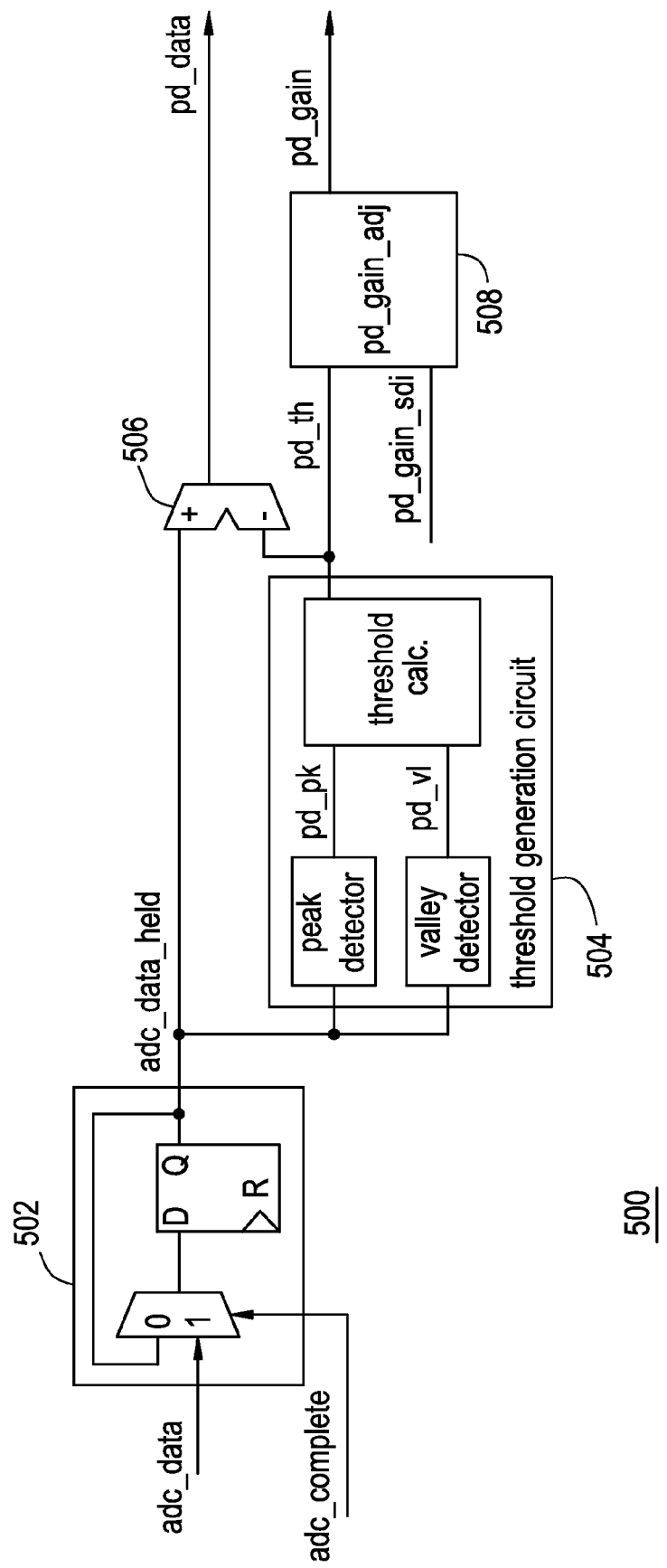
FIG. 5 is a block diagram of digital conditioning logic in accordance with the present invention.

FIG. 5 illustrates a block diagram of digital conditioning logic 500 that may be used to reduce the received ADC signal value, adc_data, to a single bit value pd_data. The digital conditioning logic 500 may comprise a digital register 502 to receive the data, adc_data, from the photodetection signal path pd_rx_top to provide a held value on the signal adc_data_held. The digital register 502 is configured to accept a new value on the adc_data signal when the adc_complete signal is asserted and to otherwise hold the last accepted value when the adc_complete signal is received. In this manner the system may disable the photodetection signal path once the data is latched to reduce system current consumption. The held data value may then be averaged, for example, by an integrate-and-dump average or other averaging methods implemented in digital logic, in the threshold generation circuit 504 to produce one or more thresholds on the signal pd_th. The held data value may then be compared, via comparator 506, to the one or more thresholds to produce a one-bit data value on the signal pd_data. It will be appreciated that the comparison operation may employ hysteresis or comparison to one or more thresholds to minimize noise on the output signal pd_data. The digital conditioning logic may further comprise a gain adjustment block pd_gain_adj 508 to set the gain of the automatic gain and low-pass filtering stage 406 in the photodetection signal path via the signal pd_gain, illustrated in FIG. 4, according to the calculated threshold values and/or according to the held data value. It is important to note that in this exemplary embodiment six bit words provide sufficient resolution over the dynamic range for blink detection while minimizing complexity.

In one exemplary embodiment, the threshold generation circuit 504 comprises a peak detector, a valley detector and a threshold calculation circuit. In this exemplary embodiment, the threshold and gain control values may be generated as follows. The peak detector and the valley detector are configured to receive the held value on signal adc_data_held. The peak detector is further configured to provide an output value, pd_pk, which quickly tracks increases in the adc_data_held value and slowly decays if the adc_data_held value decreases. The operation is analogous to that of a classic diode envelope detector, as is well-known in the electrical arts. The valley detector is further configured to provide an output value pd_vl which quickly tracks decreases in the adc_data_held value and slowly decays to a higher value if the adc_data_held value increases. The operation of the valley detector is also analogous to a diode envelope detector, with the discharge resistor tied to a positive power supply voltage. The threshold calculation circuit is configured to receive the pd_pl and pd_vl values and is further configured to calculate a mid-point threshold value pd_th_mid based on an average of the pd_pk and pd_vl values. The threshold generation circuit 504 provides the threshold value pd_th based on the mid-point threshold value pd_th_mid.

The threshold generation circuit 504 may be further adapted to update the values of the pd_pk and pd_vl levels in response to changes in the pd_gain value. If the pd_gain value increases by one step, then the pd_pk and pd_vl values are increased by a factor equal to the expected gain increase in the photodetection signal path. If the pd_gain value decreases by one step, then the pd_pk and pd_val values are decreased by a factor equal to the expected gain decrease in the photodetection signal path. In this manner the states of the peak detector and valley detectors, as held in the pd_pk and pd_vl values, respectively, and the threshold value pd_th as calculated from the pd_pk and pd_vl values are updated to match the changes in signal path gain, thereby avoiding discontinuities or other changes in state or value resulting only from the intentional change in the photodetection signal path gain.

In a further exemplary embodiment of the threshold generation circuit 504, the threshold calculation circuit may be further configured to calculate a threshold value pd_th_pk based on a proportion or percentage of the pd_pk value. In a preferred exemplary embodiment the pd_th_pk may be advantageously configured to be seven eighths of the pd_pk value, a calculation which may be implemented with a simple right shift by three bits and a subtraction as is well-known in the relevant art. The threshold calculation circuit may select the threshold value pd_th to be the lesser of pd_th_mid and pd_th_pk. In this manner, the pd_th value will never be equal to the pd_pk value, even after long periods of constant light incident on the photodiode which may result in the pd_pk and pd_vl values being equal. It will be appreciated that the pd_th_pk value ensures detection of a blink after long intervals. The behavior of the threshold generation circuit is further illustrated in FIG. 9, as discussed subsequently.

Figure 6:
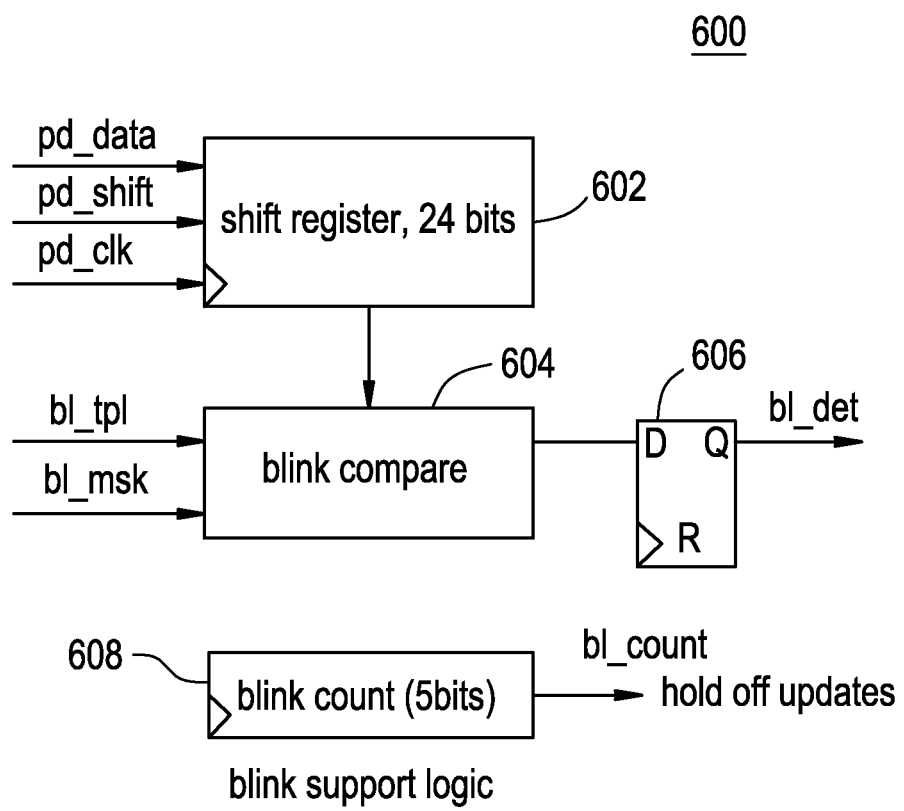
FIG. 6 is a block diagram of digital detection logic in accordance with the present invention.

FIG. 6 illustrates a block diagram of digital detection logic 600 that may be used to implement an exemplary digital blink detection algorithm in accordance with an embodiment of the present invention. The digital detection logic 600 may comprise a shift register 602 adapted to receive the data from the photodetection signal path pd_rx_top, FIG. 4, or from the digital conditioning logic, FIG. 5, as illustrated here on the signal pd_data, which has a one bit value. The shift register 602 holds a history of the received sample values, here in a 24-bit register. The digital detection logic 600 further comprises a comparison block 604, adapted to receive the sample history and one or more blink templates bl_tpl and blink masks bl_mask, and is configured to indicate a match to the one or more templates and masks on one or more output signals that may be held for later use. The output of the comparison block 604 is latched via a D flip-flop 606. The digital detection logic 600 may further comprise a counter 608 or other logic to suppress successive comparisons that may be on the same sample history set at small shifts due to the masking operations. In a preferred exemplary embodiment the sample history is cleared or reset after a positive match is found, thus requiring a full, new matching blink sequence to be sampled before being able to identify a subsequent match. The digital detection logic 600 may still further comprise a state machine or similar control circuitry to provide the control signals to the photodetection signal path and the ADC. In some exemplary embodiments the control signals may be generated by a control state machine that is separate from the digital detection logic 600. This control state machine may be part of the digital signal processing and system controller 410.

Figure 7:
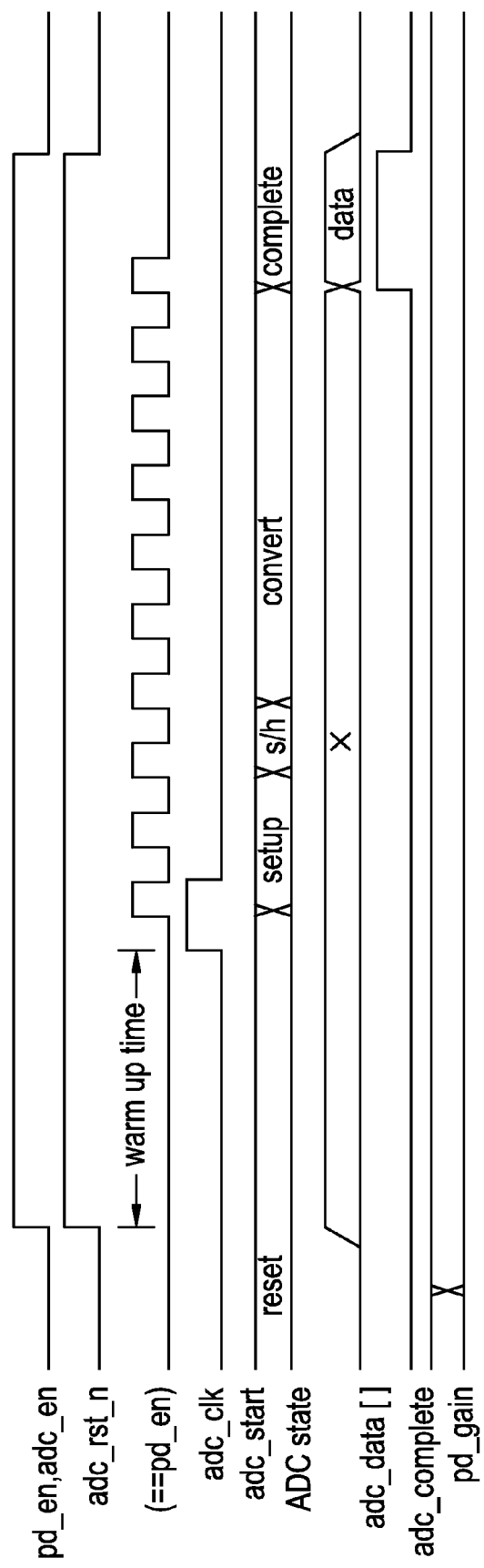
FIG. 7 is exemplary timing diagram in accordance with the present invention.

FIG. 7 illustrates a timing diagram of the control signals provided from a blink detection subsystem to an ADC 408 (FIG. 4) used in a photodetection signal path. The enable and dock signals adc_en, adc_rst_n and adc_clk are activated at the start of a sample sequence and continue until the analog-to-digital conversion process is complete. In one exemplary embodiment the ADC conversion process is started when a pulse is provided on the adc_start signal. The ADC output value is held in an adc_data signal and completion of the process is indicated by the analog-to-digital converter logic on an adc_complete signal. Also illustrated in FIG. 7 is the pd_gain signal which is utilized to set the gain of the amplifiers before the ADC. This signal is shown as being set before the warm-up time to allow the analog circuit bias and signal levels to stabilize prior to conversion.

Figure 8:
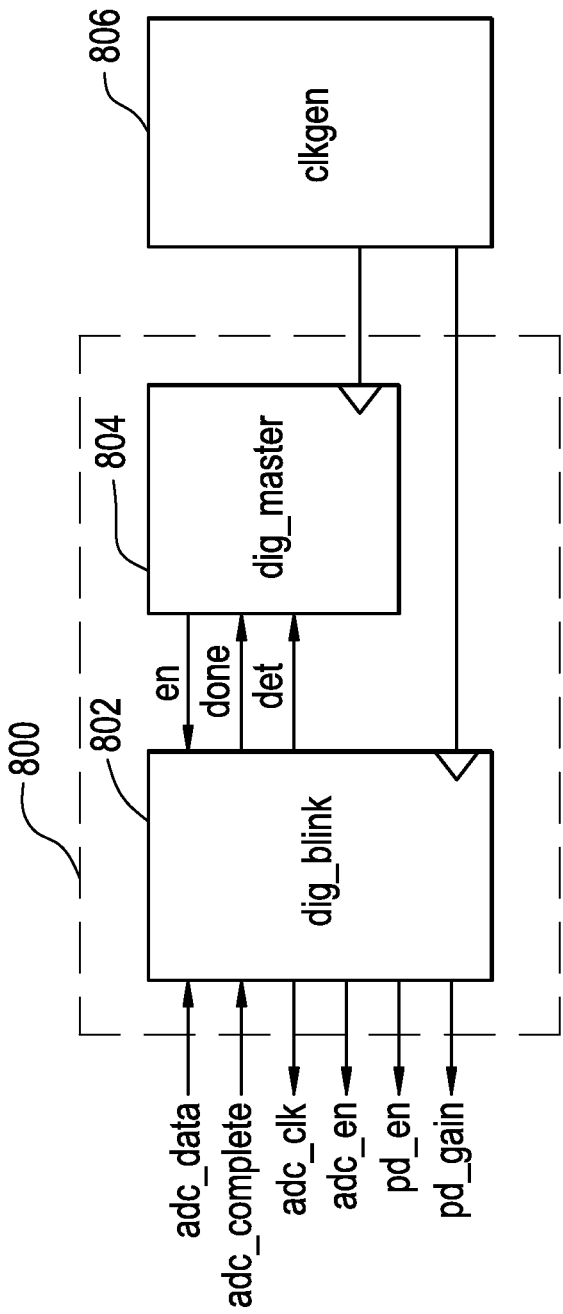
FIG. 8 is a diagrammatic representation of a digital system controller in accordance with the present invention.

FIG. 8 illustrates a digital system controller 800 comprising a digital blink detection subsystem dig_blink 802. The digital blink detection subsystem dig_blink 802 may be controlled by a master state machine dig_master 804 and may be adapted to receive dock signals from a clock generator clkgen 806 external to the digital system controller 800. The digital blink detection subsystem dig_blink 802 may be adapted to provide control signals to and receive signals from a photodetection subsystem as described above. The digital blink detection subsystem dig_blink 802 may comprise digital conditioning logic and digital detection logic as described above, in addition to a state machine to control the sequence of operations in a blink detection algorithm. The digital blink detection subsystem dig_blink 802 may be adapted to receive an enable signal from the master state machine 804 and to provide a completion or done indication and a blink detection indication back to the master state machine 804.

Figure 9A:
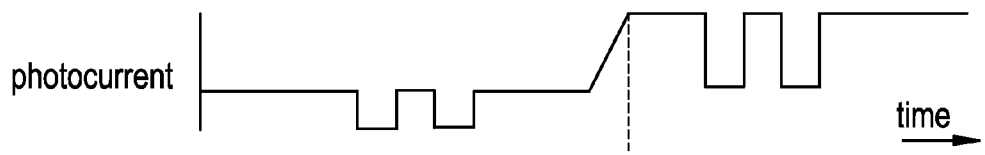
FIGS. 9A through 9G are exemplary timing diagrams for automatic gain control in accordance with the present invention.
Figure 9B:
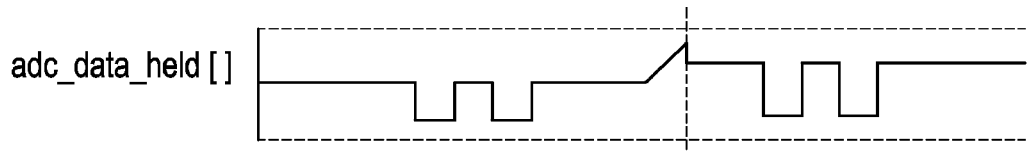
Figure 9C:
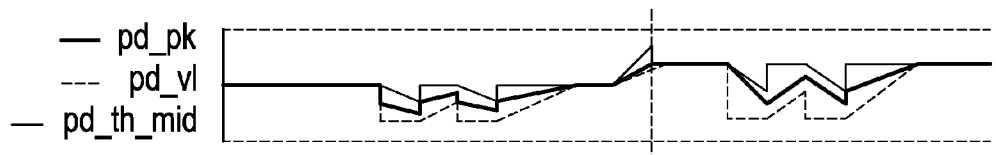
Figure 9D:
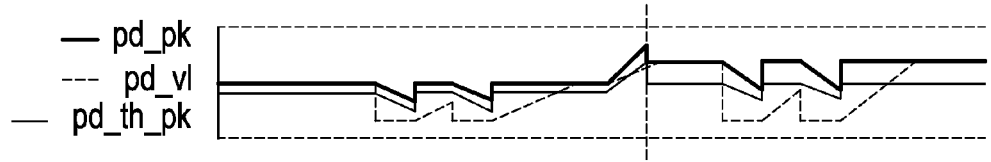
Figure 9E:
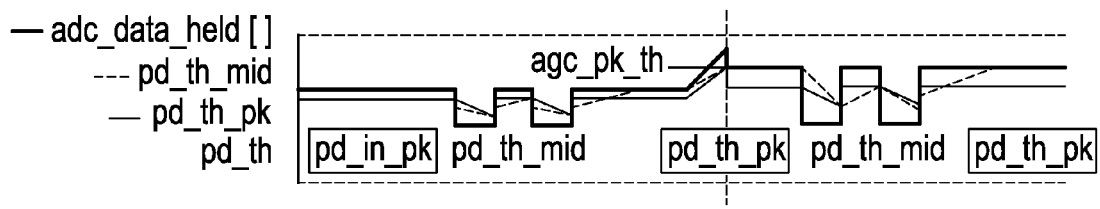
Figure 9F:
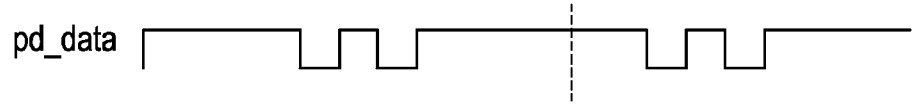
Figure 9G:
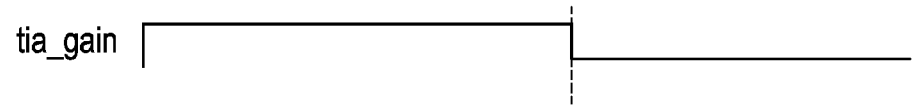

FIGS. 9A through 9G provide waveforms, to illustrate the operation of the threshold generation circuit and automatic gain control (FIG. 5). FIG. 9A illustrates an example of photocurrent versus time as might be provided by a photodiode in response to varying light levels. In the first portion of the plot, the light level and resulting photocurrent are relatively low compared to in the second portion of the plot. In both the first and second portions of the plot a double blink is seen to reduce the light and photocurrent. Note that the attenuation of light by the eyelid may not be one hundred (100) percent, but a lower value depending on the transmission properties of the eyelid for the wavelengths of light incident on the eye. FIG. 9B illustrates the adc_data_held value that is captured in response to the photocurrent waveform of FIG. 9A. For simplicity, the adc_data_held value is illustrated as a continuous analog signal rather than a series of discrete digital samples. It will be appreciated that the digital sample values will correspond to the level illustrated in FIG. 9B at the corresponding sample times. The dashed lines at the top and bottom of the plot indicate the maximum and minimum values of the adc_data and adc_data_held signals. The range of values between the minimum and maximum is also known as the dynamic range of the adc_data signal. As discussed below, the photodetection signal path gain is different (lower) in the second portion of the plot. In general the adc_data_held value is directly proportional to the photocurrent, and the gain changes only affect the ration or the constant of proportionality. FIG. 9C illustrates the pd_pk, pd_vl and pd_th_mid values calculated in response to the adc_data_held value by the threshold generation circuit. FIG. 9D illustrates the pd_pk, pd_vl and pd_th_pk values calculated in response to the adc_data_held value in some exemplary embodiments of the threshold generation circuit. Note that the pd_th_pk value is always some proportion of the pd_pk value. FIG. 9E illustrates the adc_data_held value with the pd_th_mid and pd_th_pk values. Note that during long periods of time where the adc_data_held value is relatively constant the pd_th_mid value becomes equal to the adc_data_held value as the pd_vl value decays to the same level. The pd_th_pk value always remains some amount below the adc_data_held value. Also illustrated in FIG. 9E is the selection of pd_th where the pd_th value is selected to be the lower of pd_th_pk and pd_th_mid. In this way the threshold is always set some distance away from the pd_pk value, avoiding false transitions on pd_data due to noise on the photocurrent and adc_data held signals. FIG. 9F illustrates the pd_data value generated by comparison of the adc_data_held value to the pd_th value. Note that the pd_data signal is a two-valued signal which is low when a blink is occurring. FIG. 9G illustrates a value of tia_gain versus time for these example waveforms. The value of tia_gain is set lower when the pd_th starts to exceed a high threshold shown as agc_pk_th in FIG. 9E. It will be appreciated that similar behavior occurs for raising tia_gain when pd_th starts to fall below a low threshold. Looking again at the second portion of each of the FIGS. 9A through 9E the effect of the lower tia_gain is clear. In particular note that the adc_data_held value is maintained near the middle of the dynamic range of the adc_data and adc_data_held signals. Further, it is important to note that the pd_pk and pd_vl values are updated in accordance with the gain change as described above such that discontinuities are avoided in the peak and valley detector states and values due solely to changes in the photodetection signal path gain.

Figure 10:
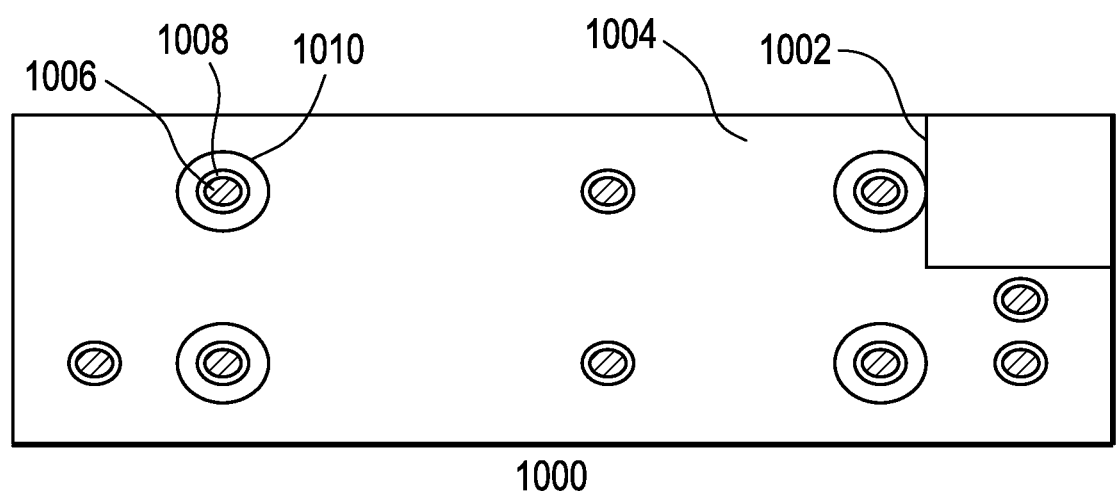
FIG. 10 is a diagrammatic representation of light-blocking and light-passing regions on an exemplary integrated circuit die in accordance with the present invention.

FIG. 10 illustrates exemplary light-blocking and light-passing features on an integrated circuit die 1000. The integrated circuit die 1000 comprises a light passing region 1002, a light blocking region 1004, bond pads 1006, passivation openings 1008, and light blocking layer openings 1010. The light-passing region 1002 is located above the photosensors (not illustrated), for example an array of photodiodes implemented in the semiconductor process. In a preferred exemplary embodiment, the light-passing region 1002 permits as much light as possible to reach the photosensors thereby maximizing sensitivity. This may be done through removing polysilicon, metal, oxide, nitride, polyimide, and other layers above the photoreceptors, as permitted in the semiconductor process utilized for fabrication or in post processing. The light-passing area 1002 may also receive other special processing to optimize light detection, for example an anti-reflective coating, filter, and/or diffuser. The light-blocking region 1004 may cover other circuitry on the die which does not require light exposure. The performance of the other circuitry may be degraded by photocurrents, for example shifting bias voltages and oscillator frequencies in the ultra-low current circuits required for incorporation into contact lenses, as mentioned previously. The light-blocking region 1004 is preferentially formed with a thin, opaque, reflective material, for example aluminum or copper already use in semiconductor wafer processing and post-processing. If implemented with metal, the material forming the light-blocking region 1004 must be insulated from the circuits underneath and the bond pads 1006 to prevent short-circuit conditions. Such insulation may be provided by the passivation already present on the die as part of normal wafer passivation, e.g. oxide, nitride, and/or polyimide, or with other dielectric added during post-processing. Masking permits light blocking layer openings 1010 so that conductive light-blocking metal does not overlap bond pads on the die. The light-blocking region 1004 is covered with additional dielectric or passivation to protect the die and avoid short-circuits during die attachment. This final passivation has passivation openings 1008 to permit connection to the bond pads 1006.

Figure 11:
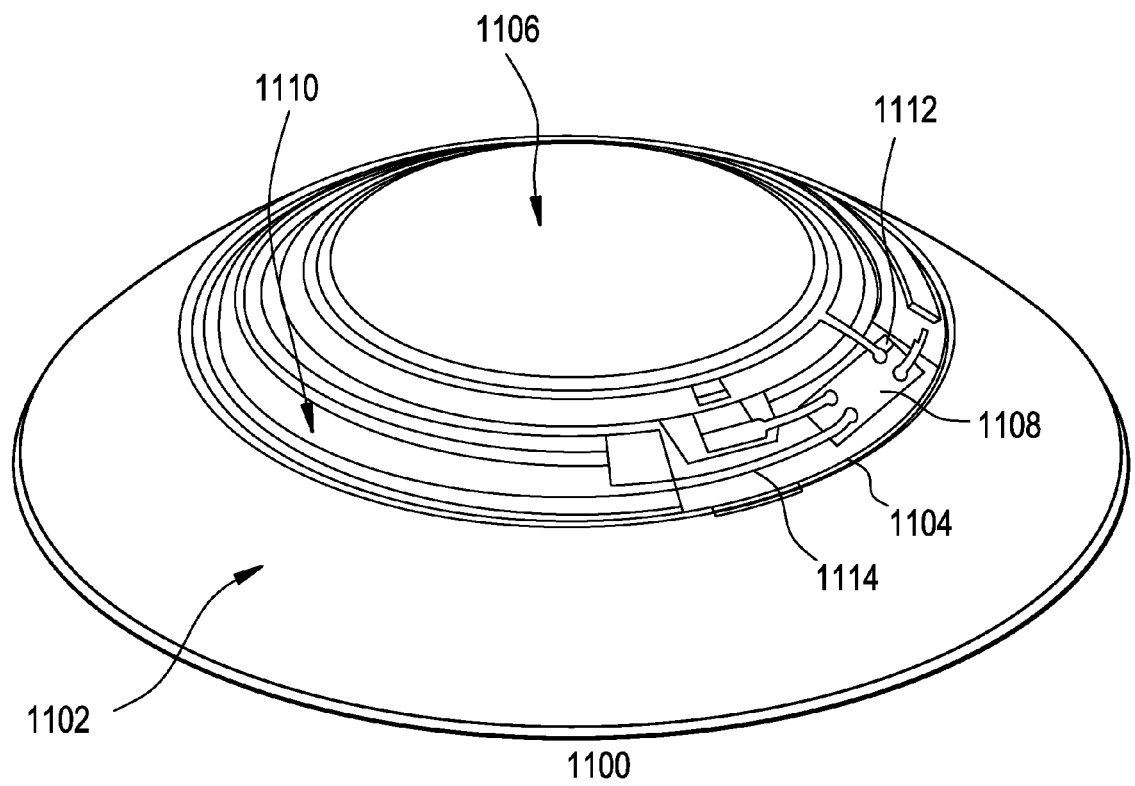
FIG. 11 is a diagrammatic representation of an exemplary electronic insert, including a blink detector, for a powered contact lens in accordance with the present invention.

FIG. 11 illustrates an exemplary contact lens with an electronic insert comprising a blink detection system in accordance with the present embodiments (invention). The contact lens 1100 comprises a soft plastic portion 1102 which comprises an electronic insert 1104. This insert 1104 includes a lens 1106 which is activated by the electronics, for example focusing near or far depending on activation. Integrated circuit 1108 mounts onto the insert 1104 and connects to batteries 1110, lens 1106, and other components as necessary for the system. The integrated circuit 1108 includes a photosensor 1112 and associated photodetector signal path circuits. The photosensor 1112 faces outward through the lens insert and away from the eye, and is thus able to receive ambient light. The photosensor 1112 may be implemented on the integrated circuit 1108 (as shown) for example as a single photodiode or array of photodiodes. The photosensor 1112 may also be implemented as a separate device mounted on the insert 1104 and connected with wiring traces 1114. When the eyelid closes, the lens insert 1104 including photodetector 1112 is covered, thereby reducing the light level incident on the photodetector 1112. The photodetector 1112 is able to measure the ambient light to determine if the user is blinking or not.

Additional embodiments of the blink detection algorithm may allow for more variation in the duration and spacing of the blink sequence, for example by timing the start of a second blink based on the measured ending time of a first blink rather than by using a fixed template or by widening the mask "don't care" intervals (0 values).

It will be appreciated that the blink detection algorithm may be implemented in digital logic or in software running on a microcontroller. The algorithm logic or microcontroller may be implemented in a single application-specific integrated circuit, ASIC, with photodetection signal path circuitry and a system controller, or it may be partitioned across more than one integrated circuit.

It is important to note that the blink detection system of the present invention has broader uses than for vision diagnostics, vision correction and vision enhancement. These broader uses include utilizing blink detection to control a wide variety of functionality for individuals with physical disabilities. The blink detection may be set up on-eye or off-eye.

In a newborn, the crystalline lens of the eye is somewhat soft and pliant making it extremely flexible and capable of a large degree of accommodation or focusing. As a person ages, the crystalline lens gradually becomes more rigid, and thus, their eyes are less able to accommodate, or bend the natural lens, to focus on objects that are relatively near to the observer. This condition is known as presbyopia.

A plus power lens may be utilized to restore the focusing power lost by the crystalline lens. The plus power lens may take the form of reading glasses, bifocal glasses or trifocal glasses. Reading glasses are easily utilized when an individual does not need refractive correction for distance. However, distant objects will be blurry when looking through reading glasses. If an individual is already wearing glasses for myopia, hyperopia and/or astigmatism, then the plus power may be added to the existing glasses in the form of a bifocal or trifocal lens. Contact lenses may also be worn to address presbyopia. In one type of such lenses, distance and near vision regions are concentrically arranged around the geometric center of the lens. Light passing though the optical zone of the lens is concentrated and focused at more than one point in the eye. These lenses are generally used in simultaneous vision mode. In simultaneous vision, portions of the lens optical zone focused for distance and near are available at the same time, focusing light from both object distances simultaneously. This is disadvantageous as image quality and image contrast may be degraded.

In another type of contact lens; namely, a segmented lens, near and distance vision regions are not concentric about the geometric center of the lens. The wearer of the segmented lenses is able to access the near vision region of the lens because the lens is constructed to allow it to translate, or move vertically relative to the pupil of the wearer's eye. This translating lens moves vertically when the person wearing the lens shifts their gaze downwardly, for example, to read. This upwardly positions the near vision portion in the center of the wearer's gaze. Substantially all of the light passing though the optical zone may be focused at a single point in the eye based on gaze.

An electronic or powered ophthalmic lens, or more particularly, an electronic or powered contact lens may, as stated above, perform any number of functions, including actuating a variable power optic. Accordingly, if a powered ophthalmic lens comprises a variable power optic, the individual wearing the lens would be able to increase his or her add power for viewing near distance objects or alternatively to decrease his or her add power for viewing far distance objects. In other words, a powered contact lens would provide an extraordinary benefit to an individual with presbyopia. Control over the variable power optic may be achieved in a number of ways. In accordance with the present invention, an emitter-detector pair sensor may be incorporated into the contact lens to automatically control the variable power optic. Emitter-detector pair sensors are devices that simply emit signals from an emitter circuit in a particular direction that bounce off an object in the signals path and are captured by a detector circuit. Obviously, if there is no object in the signals path, there will be no reflected signal to capture. From a knowledge of the energy transmitted and the time elapsed from emission to detection, the distance from the emitter-detector pair sensor to the object may be determined. This information may be input to a system controller of the powered contact lens which commands an actuator to adjust the variable power optic accordingly.

An infrared emitter-detector pair sensor may be particularly advantageous for basic object or obstacle detection and easy to implement. The present invention takes this basic circuit and implements it for incorporation into a contact lens. In accordance with another exemplary embodiment, the powered ophthalmic lens set forth herein may comprise an emitter-detector pair sensor to control a variable power optic. It is also important to note that the sensed data, in addition to or in alternate use may simply be utilized as part of a collection process rather than as a triggering event. For example, the sensed data may be collected, logged and utilized in treating medical conditions. In other words, it should also be appreciated that a device utilizing such a sensor may not change state in a manner visible to the user; rather the device may simply log data. For example, such a sensor could be used to determine if a user has the proper iris response throughout a day or if a problematic medical condition exists.

Figure 12:
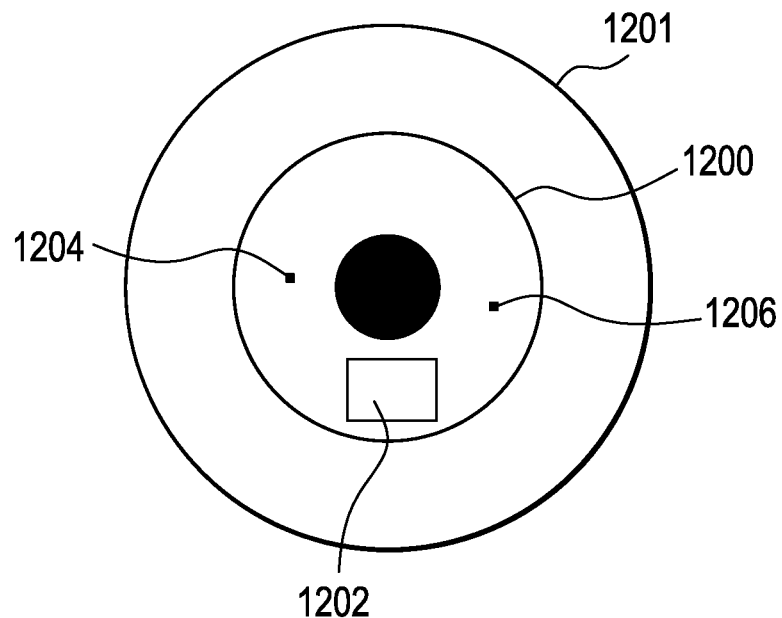
FIG. 12 is a diagrammatic representation of a directional emitter-detector pair incorporated into a powered ophthalmic lens in accordance with the present invention.

Referring now to FIG. 12, there is illustrated an exemplary electronic or powered contact lens 1200 positioned on an eye 1201. The exemplary electronic contact lens 1200 comprises a controller or control system 1202, an emitter 1204, and a detector 1206. The controller 1202 activates the emitter 1204 to send out a pulse, for example, ultrasonic or infrared radiation. The pulse may reflect off a nearby object, indicating the need for near focus, or may propagate without reflection, indicating the need for distance vision. The reflection is detected by the detector 1206 and processed by the controller 1202. In the case of ultrasonic emission, the reflection time may be used to compute the distance from the emitter 1204 to the object. For infrared emission, the presence of a reflection may indicate a nearby object, similar to proximity sensors used in towel and hand sanitizer dispensers, or triangulation may be used to determine distance. A low intensity of detected reflection, a long time to receive the reflection, and/or the lack of a reflection above ambient conditions may indicate a distant object, or more generally, the lack of a close or near object. Depending on the computed distance from the eye 1201 to the object under observation, the controller 1202 performs a particular function, for example, activating a variable-focus or variable power optic lens to the near focus state when a near object is detected. It is important to note that the pulse may comprise any suitable signal and may be specially designed to be detectable above ambient illumination, thereby increasing the sensitivity of the emitter-detector system. In addition, any suitable device may be utilized as the control system 1202. For example, the control system 1202 may comprise a microcontroller and associated memory. The control system 1202 may be implemented in hardware, software or a combination thereof.

The size and power consumption of the emitter 1204 detector 1206 pair is of critical importance for use in an ophthalmic device such as a contact or intraocular lens. As is illustrated in FIG. 12, (not to scale) the total area available for electronics on a contact lens may be only a few square millimeters, with a device thickness on the order of tens or hundreds of microns. Current capacity of onboard batteries or harvested energy may be limited to nanoamps or microamps. The emitter 1204 is thus chosen to be of an appropriate size, for example LED chips that are diced to a size of 150×150 microns or less. Dicing may require precision blade, laser, water-jet, or photolithographic etching to achieve the required small the size. The emitter the may be the bonded directly to the substrate through techniques common in the industry for LED attachment and/or the stacking. Current consumption of the emitter 1204 may be reduced by using efficient emitters to maintain sufficient photonic output power while minimizing electrical input current. Current consumption may also be reduced by using pulse and digital signal processing techniques as is known in the relevant art, for example, to design the pulse of an appropriate length and amplitude pattern to maximize detection sensitivity while lowering current or power consumption. The size and current consumption of the detector 1206 is also critical. Similar techniques to those used for the emitter 1204 may be used. The detector 1206 may be realized as a semiconductor photodiode or phototransistor, either as a standalone die or integrated with other circuits. Anti-reflective coatings, multi-layer detectors, and other techniques may be employed to increase the sensitivity of the detector 1206. The detector 1206 may be covered with a filter. It may be biased. It may be connected to an amplifier and associated signal conditioning circuitry. The biasing of the detector 1206 and/or acquisition circuitry may be pulsed at a rate corresponding to that of the detector 1206 to reduce system current consumption. Any suitable circuitry may be utilized to implement the emitter 1204 and the detector 1206 as long as it may be configured for a contact lens environment and meet the power consumption requirements.

Figure 13:
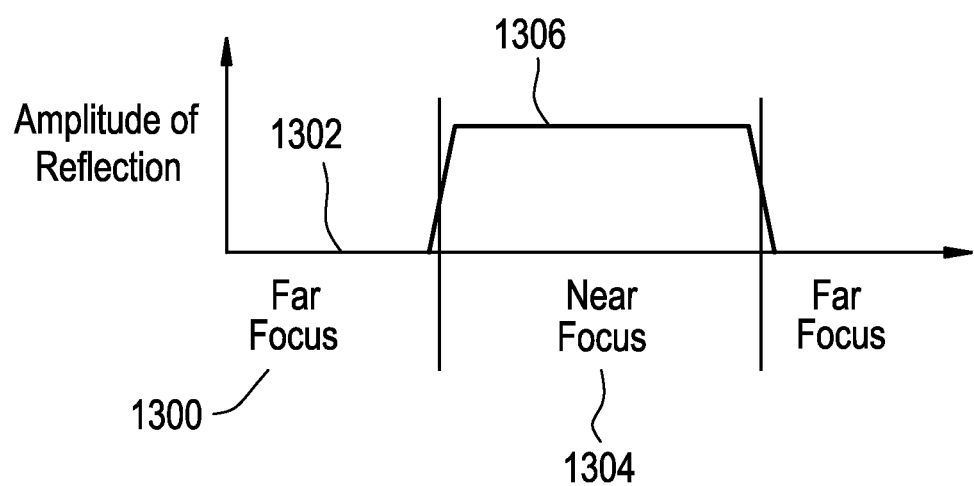
FIG. 13 is a graphical representation of the correlation between desired focal length and a signal received by a distance detecting emitter-detector pair in accordance with the present invention.

FIG. 13 graphically illustrates the correlation between reflection detected by the emitter 1204 detector 1206 pair and the focal length of the variable power optic. In a far focus state 1300 the object is distant from the eye. In the case of an infrared emitter, the amplitude of reflection 1302 for a signal emitted from the eye and detected by the eye may be low, non-existent, or comprised entirely of background noise if a nearby object is not present. In the case of an ultrasonic emission, the signal detected by the eye may be of a very low amplitude or delayed significantly from the emitted signal. Conversely, when near focus 1304 is desired on a nearby object, the amplitude of reflection may be high 1306 and/or the reflected signal may show little delay relative to the emitted signal. Thus, a sensor system relying on an emitter-detector pair may be used to determine the distance to an object of interest and hence the desired focal length.

It should be apparent that the emitter must be of sufficient amplitude and wavelength, and with a sufficiently narrow beamwidth, to reflect off near objects and be reflected to the detector. Beamwidth is important so that, for example, a handheld book is detected when a user desires near focus as opposed to the distant background. Physical coupling between the emitter-detector pair and the direction of gaze, for example, the pupil, may also be important. For example, the emitter-detector may physically track with the pupil if the entire contact lens 1201 moves with the eye. Alternately, information on the gaze position obtained from other circuitry in the contact lens 1201 may be used to direct the operation of the emitter-detector pair or as an input to received signal conditioning. For example, information on gaze could be used to activate emitter-detector pairs in certain locations of an array of emitter-detector pairs, or information on gaze could be used to select which detectors should be sampled in an array comprising many detectors. It should also be apparent that the detector should be matched to the emitter, for example, with a filter to match that of the emitter's wavelength. This practice is common in the art, to avoid spurious environmental signals from interfering with detection of the desired reflection.

It should also be apparent that digital signal processing systems, as is common in the art for non-ophthalmic applications, may be employed to optimize the performance of the emitter-detector system. For example, specific output pulse patterns may be processed by the detector to maximize the signal-to-noise ratio of the system.

In one exemplary embodiment, the electronics and electronic interconnections are made in the peripheral zone of a contact lens rather than in the optic zone. In accordance with an alternate exemplary embodiment, it is important to note that the positioning of the electronics need not be limited to the peripheral zone of the contact lens. AH of the electronic components described herein may be fabricated utilizing thin-film technology and/or transparent materials. If these technologies are utilized, the electronic components may be placed in any suitable location as long as they are compatible with the optics.

An intraocular lens or IOL is a lens that is implanted in the eye and replaces the crystalline lens. It may be utilized for individuals with cataracts or simply to treat various refractive errors. An IOL typically comprises a small plastic lens with plastic side struts called haptics to hold the lens in position within the capsular bag in the eye. Any of the electronics and/or components described herein may be incorporated into IOLs in a manner similar to that of contact lenses.

Although shown and described in what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A powered ophthalmic lens, the powered ophthalmic lens comprising: a contact lens including an optic zone and a peripheral zone; and an emitter-detector pair sensor system incorporated into the peripheral zone of the contact lens, the emitter-detector pair sensor system comprising an emitter for sending out a signal, a detector for capturing a reflection of the signal, a controller operatively associated with the emitter and detector configured to determine the distance between the contact lens and an object and output a control signal based on the determined distance, and at least one actuator configured to receive the control signal and implement a predetermined function, the emitter comprising an LED chip having a size of up 150×150 microns and the detector comprising a CMOS semiconductor.

2. The powered ophthalmic lens according to claim 1, wherein the contact lens comprises a variable-power optic incorporated into the optic zone.

3. The powered ophthalmic lens according to claim 2, wherein the actuator configures the variable-power optic for either near or for distance vision in response to the determined distance.

4. The powered ophthalmic lens according to claim 1, wherein the controller comprises a microcontroller and associated memory.

5. The powered ophthalmic lens according to claim 1, further comprising a power supply.

6. The powered ophthalmic lens according to claim 5, wherein the power supply comprises a battery.

7. A powered ophthalmic lens, the powered ophthalmic lens comprising: a contact lens; and an emitter-detector pair sensor system incorporated into the contact lens, the emitter-detector pair sensor system comprising an emitter for sending out a signal, a detector for capturing a reflection of the signal, a controller operatively associated with the emitter and detector configured to determine the distance between the contact lens and an object and output a control signal based on the determined distance, and at least one actuator configured to receive the control signal and implement a predetermined function, the emitter comprising an LED chip having a size of up 150×150 microns and the detector comprising a CMOS semiconductor photodiode.

8. The powered ophthalmic lens according to claim 7, wherein the contact lens comprises a variable-power optic incorporated into the optic zone.

9. The powered ophthalmic lens according to claim 8, wherein the actuator configures the variable-power optic for either near or for distance vision in response to the determined distance.

10. The powered ophthalmic lens according to claim 7, wherein the controller comprises a microcontroller and associated memory.

11. The powered ophthalmic lens according to claim 7, further comprising a power supply.

12. The powered ophthalmic lens according to claim 11, wherein the power supply comprises a battery.

13. A powered ophthalmic lens, the powered ophthalmic lens comprising: an intraocular lens; and an emitter-detector pair sensor system incorporated into the intraocular lens, the emitter-detector pair sensor system comprising an emitter for sending out a signal, a detector for capturing a reflection of the signal, a controller operatively associated with the emitter and detector configured to determine the distance between the intraocular lens and an object and output a control signal based on the determined distance, and at least one actuator configured to receive the control signal and implement a predetermined function, the emitter comprising an LED chip having a size of up 150×150 microns and the detector comprising a CMOS semiconductor photodiode.

* * * * *